(12) United States Patent
King et al.

(10) Patent No.: US 6,713,291 B2
(45) Date of Patent: Mar. 30, 2004

(54) ELECTRODES COATED WITH TREATING AGENT AND USES THEREOF

(76) Inventors: Alan D. King, 405 Lincoln Ave., Takoma Park, MD (US) 20912; Richard E. Walters, P.O. Box 178, Columbia, MD (US) 21045

(*) Notice: Subject to any disclaimer, the term of this patent is extended or adjusted under 35 U.S.C. 154(b) by 0 days.

(21) Appl. No.: 09/920,861

(22) Filed: Aug. 3, 2001

(65) Prior Publication Data

US 2002/0061589 A1 May 23, 2002

Related U.S. Application Data

(63) Continuation-in-part of application No. 09/889,581, filed as application No. PCT/US00/00014 on Jan. 12, 2000.
(60) Provisional application No. 60/117,755, filed on Jan. 28, 1999.

(51) Int. Cl.$^7$ ............................................. C12N 13/00
(52) U.S. Cl. ..................................................... 435/173.6
(58) Field of Search ........................... 435/173.5, 173.6

(56) References Cited

U.S. PATENT DOCUMENTS

| | | | | |
|---|---|---|---|---|
| 4,832,682 A | * | 5/1989 | Sarnoff | 604/21 |
| 5,964,726 A | * | 10/1999 | Korenstein et al. | 604/20 |
| 5,993,434 A | * | 11/1999 | Dev et al. | 604/501 |
| 6,090,617 A | * | 7/2000 | Meserol | 435/285.2 |

* cited by examiner

Primary Examiner—Jon P. Weber
(74) Attorney, Agent, or Firm—Marvin S. Townsend

(57) ABSTRACT

An object of the invention is to provide a method for delivery of macromolecules into biological cells in the tissues of a patient and includes the steps of: (a) providing electrodes (16) in an electrode assembly (12), wherein the electrodes have fixed electrode surfaces (42) which are coated with at least one static layer of electrode releasable molecules (44) to be delivered; (b) providing a waveform generator (15) for generating electric fields; (c) establishing electrically conductive pathways between the electrodes (16) and the waveform generator (15); (d) locating the electrodes (16) such that the biological cells are situated therebetween, and (g) providing electric fields in the form of pulse waveforms from the waveform generator (15) to the electrodes (16), such that molecules in the at least one static layer of the electrode releasable molecules (44) on the electrodes (16) are delivered into the biological cells. The electrode releasable molecules (44) can be either electric field separable molecules and/or solvent separable material. Another object of the invention is to provide an apparatus for carrying out the method of the invention. The static-coated electrode assembly (12) can be provided in a sterile package (24), from which the electrode assembly (12) is removed prior to use. The statically-coated electrode assembly (12) can be in a form of a disposable assembly (12) which is removable and replaceable from an electrode assembly holder (13).

24 Claims, 6 Drawing Sheets

ELECTRODES COATED WITH TREATING AGENT AND USES THEREOF

CROSS-REFERENCE TO RELATED APPLICATION

This application is a continuation-in-part of application Ser. No. 09/889,581, filed Jul. 30, 2001, which claims priority based upon copending PCT International Application No. PCT/US00/00014, filed Jan. 12, 2000, which is based upon U.S. Provisional Application Ser. No. 60/117,755, filed Jan. 28, 1999, and which was published on Aug. 3, 2000 with PCT International Publication No. WO 00/44438.

TECHNICAL FIELD

The present invention relates generally to methods and apparatus for delivery of macromolecules into cells. More specifically, the present invention provides methods and apparatus for delivering substances, such as macromolecules, e. g. deep tumor tissue treating agents, polynucleotide vaccines (DNA vaccine and/or RNA vaccine) and protein-based vaccines, into cells in tissues.

BACKGROUND ART

The first DNA vaccination procedure in the prior art was called naked DNA vaccination because a liquid solution of DNA was injected into the muscle of mice with no additives to enhance transfection. This method does transfect a few cells and does induce an immune response to the expressed antigen in mice. However, in humans and primates, the method does not work well.

In the prior art, an improvement in DNA vaccine efficiency was obtained by the use of a biolistic method for DNA delivery. The biolistic method is done by coating metal microbeads with DNA and shooting the particles into skin after accelerating the particles to a chosen velocity. This method works much better than naked DNA. Part of the reason is that the DNA coated particles are injected into the skin to a depth that increases the chance of transfecting Langerhans cells. However, the biolistic method has some disadvantages. First, it causes some skin damage that may scar in some individuals. Second, in spite of the increased efficiency, more efficiency is needed. Third, the ballistic particle remains inside the patient after treatment. In this respect, it would be desirable if a method for delivering DNA to biological cells were provided which does not cause skin damage that results in scarring. Also, it would be desirable if a method for delivering DNA to biological cells were provided which does not leave a residue of ballistic particles in cells that are treated. As a matter of interest, the following U.S. patents disclose biolistic methods: U.S. Pat. Nos. 5,036,006 and 5,478,744.

A number of additional approaches to delivering macromolecules to biological cells are disclosed in the prior art and are represented by the following U.S. patents or other publications as follows.

U.S. Pat. No. 5,019,034 of Weaver et al discloses a process for electroporation of tissues in which electrodes are placed on top of the tissue surface, such as skin, of a patient. Molecules that are used for treating the skin are placed in reservoirs on top of the skin surface, and the treatment molecules must penetrate into the skin tissues transdermally. That is, the treatment molecules must pass from outside the skin to inside the skin. Not only is the surface layer of the skin relatively impermeable, if the layers of the skin to be treated are near the basal lamina of the epidermis, then the treatment molecules must traverse considerable skin tissue before the cells to be treated are reached by the treatment molecules. Such a treatment method is inefficient for treating cells near the basal lamina. Rather than using electrodes that are placed on the skin surface and have treatment molecules pass through the skin transdermally to treat biological cells near the basal lamina of the epidermis, it would be desirable if an electroporation method were provided for delivering molecules to biological cells in the epidermis, near the basal lamina, without having the treatment molecules pass through the skin transdermally.

U.S. Pat. No. 5,273,525 of Hofmann discloses an apparatus for electroporation of drugs and genetic material into tissues which employs relatively long hollow hypodermic needle for placing the drugs and genetic material in the vicinity of the tissues to be electroporated. Whenever a hollow hypodermic is employed in a tissue, the tissue is cut with a circular cut by the hollow hypodermic needle. As a result, when a patient receives hypodermic injection, the patient has considerable pain. To avoid such a circular cut, and to avoid the considerable pain involved, it would be desirable if a method for delivering molecules to biological cells were provided which does not employ a hypodermic needle.

U.S. Pat. No. 5,318,514 of Hofmann discloses an applicator for the electroporation of drugs and genes into cells. The applicator includes a plurality of needle electrodes which can be penetrated into the skin of a patient. Material to be electroporated into the skin is retained in a fluid reservoir which wets an open cell foam elastomer carrier for the fluid. Because the material to be electroporated is retained in a fluid, in both the reservoir and the open cell foam elastomer, careful control of the amount of the material at the electrode surfaces is difficult. It is difficult to control how much fluid flows down from the reservoir and the open cell foam elastomer to the surfaces of the needle electrodes, and, thereby, it is difficult to control how much of the treatment molecules is actually present on the surfaces of the electrodes 16 as the electroporation process is being carried out on the patient. Moreover, the presence of the fluid medium can have a flushing or washing effect on the tissues that are electroporated in such a way that the electroporation process is interfered with. In these respects, it would be desirable if an electroporation method for delivering molecules to biological cells were provided which does not employ a fluid medium that flows down onto the electrodes as the electroporation process is being carried out on the patient.

Other disclosures relating to the use of electroporation to mediate gene transfer into epidermal cells are found in an article by Reiss et al entitled "DNA-mediated gene transfer into epidermal cells using electroporation" in Biochem. Biophys. Res. Commun., Vol. 137, No. 1, (1986), pages 244–249 and in an article by Titomirov entitled "In vivo electroporation and stable transformation of skin cells of newborn mice by plasmid DNA" in Biochim. Biophys. Acta., Vol. 1088, No. 1, (1991), pages 131–134.

U.S. Pat. No. 5,389,069 of Weaver discloses a method and apparatus for in vivo electroporation of tissues which employs a relatively long hollow cylindrical needle for providing treating substances deep into tissues. As mentioned above, avoiding the use hollow cylindrical needles would be desirable to avoid the pain involved therewith.

U.S. Pat. Nos. 5,580,859 and 5,589,466, both of Felgner et al, disclose a method of delivering macromolecules into muscles and skin of a patient by an injection method. Their method does not employ electroporation.

U.S. Pat. No. 5,697,901 of Eriksson discloses gene delivery into tissues by the use of a gene-carrying fluid medium that is pressurized in conjunction with hollow microneedles. Problems of control and flushing using fluid media have been discussed hereinabove. An electroporation step is not employed in the Eriksson patent. As a matter of interest, Eriksson addresses the subject of pain in two respects. There is a statement that the hollow microneedle system can be used for treating pain. There is a statement that pain in wounds can be relieved by cooling. It is noted by the present inventors herein that Eriksson does not discuss his treatment method per se as being of a pain free or reduced pain treatment method. The present inventors theorize that the pressurized fluid injection method that is employed by Eriksson is not conducive to a pain free or reduced pain treatment method. In this respect, it would be desirable to provide a gene therapy treatment method that employs micro-sized needles, but that does not employ a pressurized fluid injection step for injecting fluid into a patient.

In an article by Henry et al entitled "Microfabricated Microneedles: A Novel Approach to Transdermal Drug Delivery" in Journal of Pharmaceutical Sciences, Vol. 87, No. 8, August 1998, pages 922–925, there is a disclosure that an array of microneedles are employed to penetrate the epidermis to leave micro-sized perforations to facilitate transdermal permeability of fluid-carried treatment agents into the microperforated epidermis. Because the microneedles are inserted only a microscopic distance into the epidermis, use of the microneedles is potentially nonpainful. There is no disclosure that the microneedles are to be used as electrodes. Also, an electroporation step is not disclosed in the Henry et al article.

The following U.S. patents may be of interest for their disclosure of the use of relatively long electrodes in treating biological cells: U.S. Pat. No. 5,439,440 of Hofmann; U.S. Pat. No. 5,468,223 of Mir; U.S. Pat. No. 5,674,267 of Mir et al; U.S. Pat. No. 5,702,359 of Hofmann et al; U.S. Pat. No. 5,810,762 of Hofmann; and U.S Pat. No. 5,873,849 of Bernard. It is noted that none of the patents listed in this paragraph disclose the use of relatively long electrodes which have fixed electrode surfaces which are coated with a static layer of electrode releasable molecules for treating the biological cells either when an electric field is applied to the electrodes or when the static layer dissolves off of the electrodes in a solvent near the biological cells.

Further with respect to the issue of reduced pain treatment, it is noted that two important electrical parameters in electroporation are closely related to a perceived pain in vivo. One parameter is absolute voltage experienced by the in vivo tissue. Another parameter is the pulse width experienced by the in vivo tissue. In these respects, it would be desirable to provide an electroporation method for delivering molecules to biological cells which applies relatively low absolute voltage to cells undergoing electroporation and which can be used, if desired, to apply pulses having relatively short pulse width to the cells undergoing electroporation.

Still other features would be desirable in a method and apparatus for delivery of macromolecules into epidermal cells. For example, when electrodes are penetrated into the epidermis, the conductive base electrode portions and the conductive tips of the electrodes may exhibit electrical characteristics which are undesirable with respect to the electroporation process in general and the biological cells that are treated in particular. In this respect, it would be desirable if a method and apparatus for delivery of macromolecules into epidermal cells were provided which render nonconductive the base portions and tip portions of the electrodes.

Once electrode assemblies having a plurality of needle electrodes have been employed on a patient, it may be a difficult task to clean and sterilize them for a subsequent use. In this respect, it would be desirable if a method and apparatus for delivery of macromolecules into cells were provided in which the electrode assemblies are disposable.

When disposable electrode assemblies are employed, it would be desirable if the disposable electrode assemblies are packaged in sterile packaging.

Thus, while the foregoing body of prior art indicates it to be well known to use electroporation to deliver molecules to biological cells, the prior art described above does not teach or suggest a method and apparatus for delivery of macromolecules into cells which has most of the following combination of desirable features: (1) does not cause skin damage that results in scarring; (2) does not leave a residue of ballistic particles in cells that are treated; (3) provides an electroporation method for delivering molecules to biological cells in the epidermis, near the basal lamina, without having the treatment molecules pass through the skin transdermally; (4) does not employ a hypodermic needle; (5) does not employ a fluid medium that flows down onto the electrodes as the electroporation process is being carried out on the patient; (6) does not employ a pressurized fluid injection step for injecting fluid into a patient; (7) applies relatively low absolute voltage to cells undergoing electroporation; (8) if desired, can be used to apply pulses having relatively short pulse width to the cells undergoing electroporation; (9) renders the base portions and tip portions of the electrodes nonconductive; (10) provides disposable electrode assemblies; (11) provides electrode assemblies which are packaged in sterile packaging: and (12) permits treatment of tissues using coated long electrodes which have electrode releasable material which includes a tissue treating agent. The foregoing desired characteristics are provided by the unique electrodes coated with treating agent and uses thereof, of the present invention as will be made apparent from the following description thereof. Other advantages of the present invention over the prior art also will be rendered evident.

DISCLOSURE OF INVENTION

It is noted that aspects of the invention have been disclosed in copending PCT International Application No. PCT/US00/00014, filed Jan. 12, 2000, which is based upon copending U.S. Provisional Application Ser. No. 60/117, 755, filed Jan. 28, 1999. The PCT International Application No. PCT/US00/00014 was published on Aug. 3, 2000 with PCT International Publication Number WO 00/44438. In addition to currently disclosing some of those aspects of the invention previously disclosed in the above-mentioned PCT and U.S. Provisional applications, the present application discloses additional invention aspects.

In accordance with one aspect of the invention, a method is provided for delivery of molecules into biological cells which includes the steps of:

(a) providing electrodes in an electrode assembly, wherein the electrodes have a fixed electrode surface, (b) coating the fixed electrode surfaces of the electrodes with at least one static layer of electrode releasable molecules to be delivered, (c) attaching the electrode assembly having the statically coated electrodes to an electrode assembly holder, (d) providing a waveform generator for generating electric fields, (e) establishing electrically conductive pathways between the electrodes and the waveform generator, (f) locating the electrodes such that the biological cells are situated therebetween, and (g) providing electric fields in the form of pulse waveforms from the waveform generator to the electrodes, such that molecules in the at least one static layer of the electrode releasable molecules on the electrodes are delivered into the biological cells.

On the one hand, when the static layer of electrode releasable molecules does not include solvent separable material, then substantially all of the static layer of electrode releasable molecules are electric field separable molecules. In such a case, the electric field separable molecules are both driven off of the electrodes and delivered into the biological cells by the applied electric fields.

On the other hand, when the static layer of electrode releasable molecules does include solvent separable material, such as solvent separable solid material, then the static layer of electrode releasable molecules includes both solvent separable solid material and electric field separable molecules. In such a case, a solvent dissolves the solvent separable material thereby releasing the electric field separable molecules from the electrode, and the electric field separable molecules are delivered into the biological cells by the applied electric fields. The solvent includes body fluids which are present in body tissues.

Often, the electrode releasable molecules are in a form of a static coating on the fixed electrode surface. In this respect, the term "static" means that the coating remains stationary on the fixed electrode surface when either not in tissues or not under the influence of an electric field. However, such a static coating moves off of the fixed electrode surface either when it is dissolved off of the fixed electrode surface or when it is driven off of the fixed electrode surface under the influence of either a solvent or a suitable electric field, respectively.

A number of benefits can be realized by employing the static coated electrodes of the present invention. For example, a pre-measured quantity of a static layer of electrode releasable molecules can be retained on the fixed electrode surfaces. Such a pre-measured quantity of the static layer of electrode releasable molecules can serve as a pre-measured dose of material to be delivered to the biological cells. Moreover, the static coated electrodes can be coated with a concentrated quantity of the electrode releasable molecules. In addition, the static coated electrodes can be pre-packaged so that when they are removed from their package, they are rapidly ready for use, without the need for conventional preparatory steps such as dilution and hypodermic injection.

Also, in accordance with aspects of the present invention, an electrode includes an electrode underbody and a fixed electrode surface which lies on top of the electrode underbody. The fixed electrode surface can be implemented in a wide variety of embodiments. For example, most simply, the simple surface of the electrode itself can serve as the fixed electrode surface which lies on top of the electrode underbody. The fixed electrode surface can be a smooth electrode surface, can be an oxidized metal surface (e. g. oxides of silver, nickel, and copper), can include fixed metal particles, and can be a roughened surface.

Also, in accordance with aspects of the present invention, the electrode releasable material on the fixed electrode surface can be in a form of a gel coating, a solid layer of nonpolymeric material, and a polymer layer.

Varieties of the fixed electrode surface and the static, electrode releasable material can be mixed and matched.

Some specific examples of combinations of the fixed electrode surface and the electrode releasable material include: a fixed electrode surface having metal oxides and electrode releasable material including DNA; a fixed electrode surface being a smooth surface and the electrode releasable material in the form of a solid coating; a fixed electrode surface having an etched rough surface and the electrode releasable material as either a solid nonpolymeric layer, a gel layer, or a polymeric layer.

The pulse waveforms may be provided by applying a sequence of at least three single, operator-controlled, independently programmed, DC electrical pulses, to the biological cells. The sequence of at least three DC electrical pulses has one, two, or three of the following characteristics (a) at least two of the at least three pulses differ from each other in pulse amplitude, (b) at least two of the at least three pulses differ from each other in pulse width, and (c) a first pulse interval for a first set of two of the at least three pulses is different from a second pulse interval for a second set of two of the at least three pulses.

Additionally, the method can include a step of providing the electrode assembly holder with electrically conductive pathways between the electrode assembly and the waveform generator.

In addition, the method can include a step of providing the electrode assembly in a sterile package. In such a case, the electrode assembly is removed from the sterile package prior to use.

Further, the method can include the steps of providing the electrodes with electrically insulated outer surface electrode tip portions and electrically insulated outer surface electrode base portions.

The molecules in the at least one static layer of molecules in the electrode coating preferably include macromolecules. The macromolecules in the electrode coating can include a tissue treating agent, a polynucleotide vaccine (DNA vaccine and/or RNA vaccine), or a protein-based vaccine, among others.

With a variation of the method of the invention, the molecules can be delivered to Langerhans cells in epidermal tissue of a patient with reduced sensation (reduced pain or nearly painless or pain free) to the patient. To provide reduced sensation delivery of molecules to the patient, the following conditions are maintained (a) the pulse waveforms have an absolute applied voltage in a range of 0.1 to 300 volts; (b) the electrodes of opposite polarity are separated by a separation distance in a range of from 50 to 500 microns; and (c) the electrodes are penetrated into the epidermal tissue a distance up to and slightly beyond the basal lamina layer of the epidermal tissue.

With another variation of the method of the invention, the molecules can be delivered to a tissue which is deeply located under healthy tissue. With such a variation of the method of the invention, the electrodes are long enough to penetrate through the healthy tissue and into the tumor. The fixed electrode surface portions of the electrodes that penetrate the tumor are coated with electrode releasable material that includes a deep tumor tissue treating agent.

The pulse waveforms which drive the molecules of the electrode releasable coating molecules off of the electrodes are electrophoresis waveforms. The pulse waveforms which deliver the driven-off molecules into the biological cells are electroporation waveforms. For a static layer of electric field separable molecules, common pulse waveforms both drive the coating molecules off of the electrodes and deliver the driven-off molecules into the biological cells.

The biological cells can be in vivo, ex vivo, or in vitro. More specifically, the biological cells can be in epidermal tissue and can be Langerhans cells in the epidermal tissue. Also, the biological cells can be in deep tissues, and can be in tumors in deep tissues.

In accordance with another aspect of the invention, an apparatus is provided for delivery of molecules into biological cells and includes a waveform generator which provides pulse waveforms. An electrode assembly holder is provided, and an electrode assembly is mechanically supported by the electrode assembly holder. The electrode assembly holder is also electrically connected to the waveform generator through electrically conductive pathways. The electrode assembly includes electrodes which are coated with at least one static layer of molecules to be delivered into the biological cells.

The electrode assembly can be removable and replaceable from the electrode assembly holder. In this respect, the electrode assembly includes electrode-assembly-conductive strips. The electrode assembly holder includes holder conductors which are registrable with the electrode-assembly-conductive strips when the electrode assembly is mechanically connected to the electrode assembly holder. Also, the electrode assembly holder includes electrically conductive pathways between the holder conductors and the waveform generator.

With the apparatus, a sterile package can be provided for the electrode assembly. The sterile package is removed from the electrode assembly after the electrode assembly is mechanically supported by the electrode assembly holder and is electrically connected to the waveform generator.

With the apparatus, if desired, the waveform generator provides pulse waveforms which include a sequence of at least three single, operator-controlled, independently programmed, DC electrical pulses, to the biological cells. The sequence of at least three DC electrical pulses has one, two, or three of the following characteristics (a) at least two of the at least three pulses differ from each other in pulse amplitude, (b) at least two of the at least three pulses differ from each other in pulse width, and (c) a first pulse interval for a first set of two of the at least three pulses is different from a second pulse interval for a second set of two of the at least three pulses.

The electrodes can include electrically insulated outer surface electrode tip portions and electrically insulated outer surface electrode base portions. The electrodes are coated with at least one static layer of molecules, which may include macromolecules, which may include a tissue treating agent, a polynucleotide vaccine (a DNA vaccine and/or a RNA vaccine) and/or a protein-based vaccine.

The static layer of electrode releasable macromolecules on the electrodes (e. g. a tissue treating agent, a polynucleotide vaccine, or a protein-based vaccine, among others) can be in a variety of forms prior to using the electrodes on a patient. More specifically, the static layer of macromolecules can be in a solid form, coating the solid electrodes. Also, the static layer of macromolecules can be in a gel form or can be in a form of a liquid fixed on a fixed surface matrix of the electrodes. The fixed surface matrix can be solid surface particles (e. g. metal particles), a liposome matrix, or a solid polymer matrix.

In accordance with yet another aspect of the invention, a packaged sterile electrode assembly is provided which includes a sterile electrode assembly which includes electrodes which are coated with at least one static layer of molecules to be delivered into biological cells. The electrode assembly includes electrode-assembly-conductive strips for connection to complementary electrically conductive pathways leading to the waveform generator. In addition, an internally sterile package encloses the sterile electrode assembly contained therein.

With the packaged sterile electrode assembly, the electrodes can include electrically insulated outer surface electrode tip portions and electrically insulated outer surface electrode base portions.

With the packaged sterile electrode assembly, the electrodes are coated with macromolecules which can include a solid phase polynucleotide (DNA vaccine and/or RNA vaccine) and/or a solid phase protein-based vaccine. Also, the polynucleotide vaccine or protein-based vaccine can be in a gel form or can be in a form of a liquid fixed on a fixed surface matrix of the electrodes, prior to using the electrodes on a patient. The fixed surface matrix can be solid surface particles (e. g. metal particles), a liposome matrix, or a solid polymer matrix.

In accordance with the invention, transfection of cells with DNA in vivo, using electric field mediated transfection, is an efficient process. Additionally, electric fields can be used for the delivery of other macromolecules such as RNA and proteins into cells. In the prior art, the electric field delivery has one disadvantage, that being the pain induced by the high voltage electrical pulses required for the transfection. In contrast, as described herein, a method is provided for delivering macromolecules (DNA, RNA, and protein) to cells, in tissues in vivo, using painless (or nearly painless) and efficient electric field mediated delivery.

A number of applications of the method and apparatus for delivery of macromolecules into cells, of the invention, are contemplated. Briefly, such applications include treating organ tissues, polynucleotide vaccination, protein vaccination, and gene therapy For treating deep tumor tissues, it is important to maximize delivery of the deep tumor tissue treating agent to the tumor tissue and to minimize deliver of the agent to healthy tissue.

For DNA vaccination, there are two overriding requirements. One is gene expression in vivo and the other is that antigen-presenting cells must either obtain antigen from a nearby, transfected cell or express the antigen themselves. The highest concentration of accessible antigen presenting cells resides in the skin as cells called Langerhans cells. These cells are part of a very effective group of antigen presenting cells called dendritic cells. Electroporation is a viable alternative method for transfecting selected cells in vivo.

Proteins also can be introduced into cells using electric field mediated delivery. In conventional vaccination, proteins are delivered outside cells using a hypodermic needle. This type of delivery is inefficient in inducing a cell mediated cytotoxic lymphocyte immune response. Some infectious diseases require a cytotoxic lymphocyte response as a component of the immune response for efficient clearance of the infection. Delivery of proteins into cells promotes the induction of that response.

Delivery of therapeutic genetic medicine into cells for the purpose of making those cells express a missing protein is the basis of gene therapy. Using relatively short electrodes of the invention, the method and apparatus of the invention can be used to deliver therapeutic DNA into cells on the surface of any accessible organ in addition to the skin. Using relatively long electrodes of the invention, the method and apparatus of the invention can be used to deliver therapeutic DNA into cells deep into tissues and organs.

The method of the invention can be used in a method for painless, effective delivery of macromolecules to epidermal tissues, in vivo, for the purpose of vaccination (or treatment), DNA vaccination, gene therapy, or other reasons.

An electrode with at least one of two characteristics is used for delivery of macromolecules into cells in epidermal tissue. One of the two characteristics is an electrode length short enough that it does not penetrate to a depth in tissue with nerve endings. Another characteristic is that interelectrode distances are small enough to allow pulse parameters (voltage and pulse width) to be used that are painless. Only one or the other of these characteristics is needed in any given epidermal application, however, they may be used together.

The above brief description sets forth rather broadly the more important features of the present invention in order that the detailed description thereof that follows may be better understood, and in order that the present contributions to the art may be better appreciated. There are, of course, additional features of the invention that will be described hereinafter and which will be for the subject matter of the claims appended hereto.

In this respect, before explaining preferred embodiments of the invention in detail, it is understood that the invention is not limited in its application to the details of the construction and to the arrangements of the components set forth in the following description or illustrated in the drawings. The invention is capable of other embodiments and of being practiced and carried out in various ways. Also, it is to be understood, that the phraseology and terminology employed herein are for the purpose of description and should not be regarded as limiting.

As such, those skilled in the art will appreciate that the conception, upon which disclosure is based, may readily be utilized as a basis for designing other structures, methods, and systems for carrying out the several purposes of the present invention. It is important, therefore, that the claims be regarded as including such equivalent constructions insofar as they do not depart from the spirit and scope of the present invention.

In view of the above, it is an object of the present invention to provide a new and improved method and apparatus for delivery of macromolecules into cells which does not cause skin damage that results in scarring.

Another object of the present invention is to provide a new and improved method and apparatus for delivery of macromolecules into cells which does not leave a residue of ballistic particles in cells that are treated.

Even another object of the present invention is to provide a new and improved method and apparatus for delivery of macromolecules into cells that provides an electroporation method for delivering molecules to biological cells in the epidermis, near the basal lamina, without having the treatment molecules pass through the skin transdermally.

Still a further object of the present invention is to provide a new and improved method and apparatus for delivery of macromolecules into cells which does not employ a hypodermic needle.

Yet another object of the present invention is to provide a new and improved method and apparatus for delivery of macromolecules into cells that does not employ a fluid medium that flows down onto the electrodes as the electroporation process is being carried out on the patient.

Still another object of the present invention is to provide a new and improved method and apparatus for delivery of macromolecules into cells which does not employ a pressurized fluid injection step for injecting fluid into a patient.

Yet another object of the present invention is to provide a new and improved method and apparatus for delivery of macromolecules into cells that applies relatively low absolute voltage to cells undergoing electroporation.

Still a further object of the present invention is to provide a new and improved method and apparatus for delivery of macromolecules into cells that can be used, if desired, to apply pulses having relatively short pulse width to the cells undergoing electroporation.

Yet another object of the present invention is to provide a new and improved method and apparatus for delivery of macromolecules into cells which renders the base portions and tip portions of the electrodes nonconductive.

Still a further object of the present invention is to provide a new and improved method and apparatus for delivery of macromolecules into cells that provides disposable electrode assemblies.

Yet another object of the present invention is to provide a new and improved method and apparatus for delivery of macromolecules into cells which electrode assemblies are packaged in sterile packaging.

Still another object of the present invention is to provide a new and improved method and apparatus for delivery of macromolecules into cells which permit treatment of tissues using coated long electrodes which have electric field separable material which includes a tissue treating agent.

These together with still other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there are illustrated preferred embodiments of the invention.

BRIEF DESCRIPTION OF DRAWINGS

The invention will be better understood and the above objects as well as objects other than those set forth above will become more apparent after a study of the following detailed description thereof. Such description makes reference to the annexed drawing wherein.

MODES FOR CARRYING OUT THE INVENTION

Figure 1:
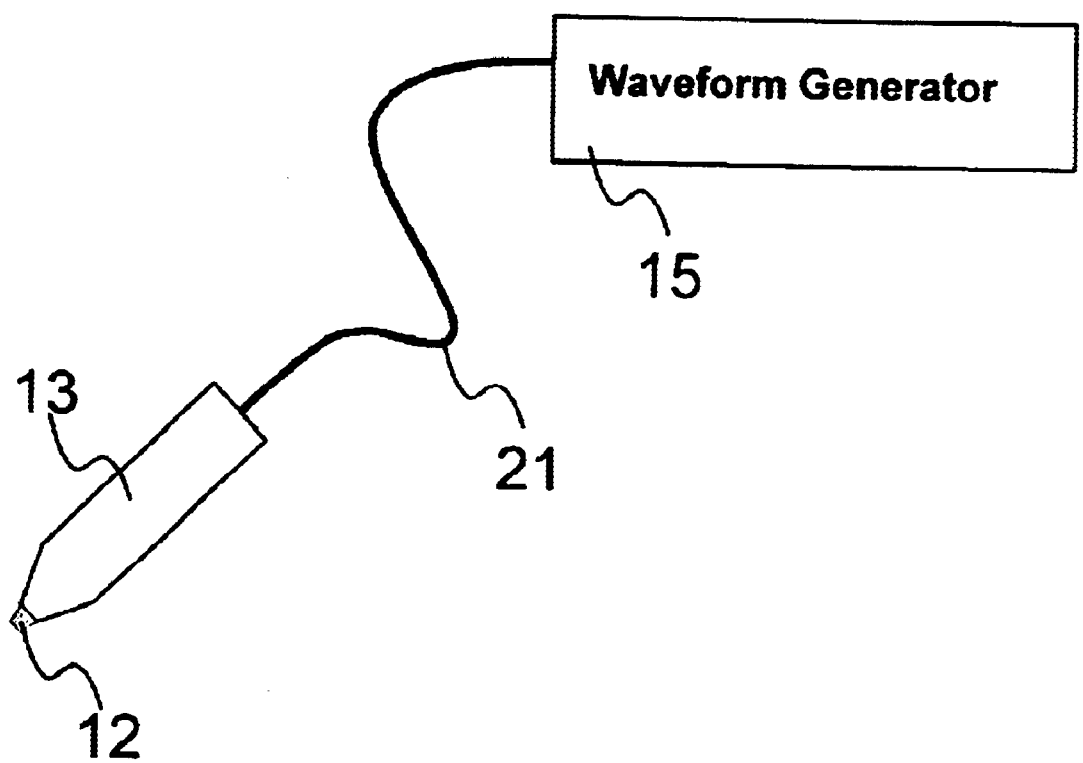
FIG. 1 is a schematic illustration of the overall apparatus of the invention.

A method and apparatus are provided for delivery of macromolecules into cells, and with reference to the drawings, said method and apparatus are described below. The method for delivery of molecules into biological cells employs the apparatus set forth and includes the steps of (a) providing electrodes 16 in an electrode assembly 12, wherein the electrodes have a fixed electrode surface 42, (b) coating the fixed electrode surfaces 42 of the electrodes 16 with at least one static layer of electrode releasable molecules 44 to be delivered, (c) attaching the electrode assembly 12 having the statically coated electrodes 16 to an electrode assembly holder 13, (d) providing a waveform generator 15 for generating electric fields, (e) establishing electrically conductive pathways between the electrodes 16 and the waveform generator 15, (f) locating the electrodes 16 such that the biological cells are situated therebetween, and (g) providing electric fields in the form of pulse waveforms from the waveform generator 15 to the electrodes 16, such that molecules in the at least one static layer of the electrode releasable molecules 44 on the electrodes 16 are delivered into the biological cells.

Figure 5:
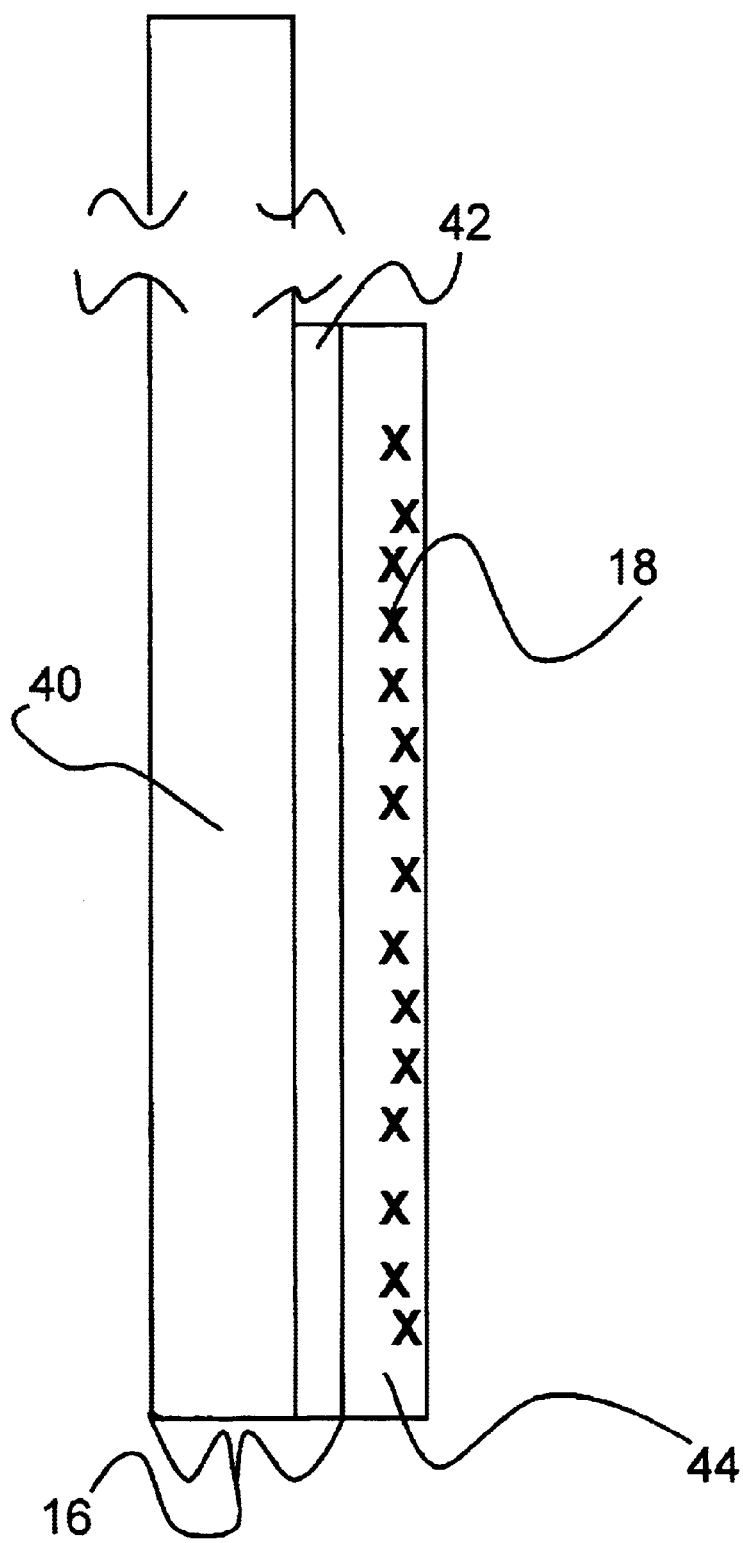
FIG. 5 schematically shows an electrode which has a fixed electrode surface that is coated with a static layer of electrode releasable molecules.

Referring to FIG. 5, an electrode 16 includes an electrode underbody 40 and a fixed electrode surface 42 which lies on top of the electrode underbody 40. A static layer of electrode releasable molecules 44 is located on top of the fixed electrode surface 42. It is noted, however, that in different embodiments, the fixed electrode surface 42 and the static layer of electrode releasable molecules 44 can be intermingled.

In some embodiments of the invention, the static layer of electrode releasable molecules 44 is homogeneous and includes substantially only electric field separable molecules. In other embodiments, the electrode releasable molecules 44 include only a solvent separable material. In still other embodiments, the electrode releasable molecules 44 include both electric field separable molecules and solvent separable material. Generally, the solvent separable material is in a solid state. Alternatively, the solvent separable material can be in a gel state.

With reference to FIG. 4, in one variation of the method, using long needle electrodes 34 which are coated with a static layer of electrode releasable molecules 44, e. g. macromolecules 18 which include a deep tumor tissue treating agent, a deep tumor tissue 38 is treated with the macromolecules 18 which are driven off of the long needle electrodes 34 by an imposed electric field.

With reference to FIG. 4, a specific example of the above procedure is the use of plasmids expressing lymphokines for cancer immunotherapy. In one example, plasmids expressing interleukin-2 are coated onto the long needles 34 using the described method. More specifically, the macromolecules 18 in FIG. 4 include the plasmids expressing interleukin-2. The long needles 34 are then inserted through healthy tissue 33 into selected tumor tissue 38. Then, the electrophoretic and electroporation pulses administered. This method is used to induce a local immune response to the tumor tissue 38 in an effort to generate a generalized immune response. Plasmids expressing other lymphokines can be used in this procedure. Examples are interleukin-12, interleukin-4, interferon-gamma and a variety of others. Plasmids expressing other immune system molecules such as co-stimulatory molecules or adhesion molecules can also be used.

In another variation of the method, referring to FIG. 2, the statically-coated molecules are delivered with reduced sensation in a patient to Langerhans cells 22 in the epidermis 20 of a patient. The pulse waveforms have an absolute applied voltage in a range of from 0.1 to 300 volts. Electrodes 16 of opposite polarity are separated by a separation distance in a range of from 50 to 500 microns. The statically-coated electrodes 16 are penetrated into the epidermal tissue up to and slightly beyond the basal lamina layer of the epidermal tissue.

The pulse waveforms which drive the coating molecules off of the electrodes 16 are electrophoresis waveforms. The electrophoresis waveforms can be in a range of from 0.1 to 100 volts/cm. The pulse waveforms which deliver the driven-off molecules into the biological cells are electroporation waveforms. The electroporation waveforms can be in a range of from 100 to 10,000 volts/cm. Common pulse waveforms both drive the coating molecules off of the electrodes 16 and deliver the driven-off molecules into the biological cells.

The biological cells to which the molecules are delivered can be in vivo, ex vivo, or in vitro. More specifically, as shown in FIG. 2, the biological cells can be in the epidermis 20 (epidermal tissue) and can be Langerhans cells 22 in the epidermal tissue.

The statically-coated molecules driven off of the electrodes 16 by electrophoresis electrical pulses are delivered to the cells by electroporation pulses. In accordance with an exemplary protocol, the pulse waveforms are provided by the waveform generator 15 by applying a sequence of at least three single, operator-controlled, independently programmed, DC electrical pulses, to the biological cells. The sequence of at least three DC electrical pulses has one, two, or three of the following characteristics (1) at least two of the at least three pulses differ from each other in pulse amplitude, (2) at least two of the at least three pulses differ from each other in pulse width, and (3) a first pulse interval for a first set of two of the at least three pulses is different from a second pulse interval for a second set of two of the at least three pulses.

The electrode assembly holder 13 is provided with electrically conductive pathways, which includes conductors 21, between the electrode assembly 12 and the waveform generator 15.

The electrode assembly 12 can be provided in a sterile package 24 which is removed from the electrode assembly 12 prior to use.

Preferably, for electrodes 16 used with epidermal tissue, the electrodes 16 have conical tips, whereby they are referred to as needle electrodes. The electrodes 16 can be provided with electrically insulated outer surface electrode tip portions 17 and electrically insulated outer surface electrode base portions 19. The electrically insulated outer surface electrode base portions 19 minimize current flowing across the upper skin surface when the pulse voltage is applied. Moreover, DNA binds poorly to the electrically insulated outer surface electrode base portions 19. The outer surface area of the electrodes 16 between the electrically insulated outer surface electrode tip portions 17 and the electrically insulated outer surface electrode base portions 19 does not have an outer insulation layer and is a good surface for DNA binding. The outer surface areas between the electrically insulated outer surface electrode tip portions 17 and the electrically insulated outer surface electrode base portions 19 is conductive and can be referred to as an active electrode area. The electrically insulated outer surface electrode tip portions 17 prevent large local electric field intensity which may cause burning in the tissue.

An electrode assembly 12 that is suitable for delivering DNA vaccines to Langerhans cells 22 in the epidermis 20 of the forearm has the following characteristics:

(a) electrode length—130 microns
(b) electrode material resistivity—less than 0.1 ohm-cm
(c) insulation at tip—extending upward 10 microns from tip end
(d) insulation at base—extending downward 55 microns from electrode carrier
(e) electrode tip flatness—less than 1 square micron
(f) electrode diameter at base—43 microns
(g) electrode spacing in a conductive row—130 microns
(h) number of electrodes in a conductive row—35
(i) space between conductive rows—260 microns (2×130)
(j) number of conductive rows—25.

For epidermal applications, the lengths of the electrodes 16 are determined by the thickness of the epidermis 20. The thickness of the epidermis 20 varies in different parts of the human body. For example, the thickness of the epidermis 20 on the medial forearm or the lateral upper arm above the deltoid muscle is considerably thinner than the thickness of the epidermis 20 on the heel or sole of the foot.

Referrring to FIG. 5, molecules in the static layer of electric field separable molecules 44 preferably include macromolecules 18. The macromolecules 18 in the electrode coating can include a deep tumor tissue treating agent, a polynucleotide vaccine (e.g a DNA vaccine or an RNA vaccine), and/or a protein-based vaccine. The polynucleotide vaccine and the protein-based vaccine can be in the form of a solid phase DNA vaccine or protein-based vaccine applied to the electrodes 16. Also, the polynucleotide vaccine or protein-based vaccine can be in a gel form or can be in a form of a liquid fixed on a fixed surface matrix of the electrodes. The fixed surface matrix can be solid surface particles (e. g. metal particles), a liposome matrix, or a solid polymer matrix.

Preferably, the electrode assembly 12 is removable and replaceable from the electrode assembly holder 13. The electrode assembly 12 includes electrode-assembly-conductive strips. The electrode assembly holder 13 includes holder conductors which are registrable with the electrode-assembly-conductive strips when the electrode assembly 12 is mechanically connected to the electrode assembly holder 13. The electrode assembly holder 13 includes electrically conductive pathways between the holder conductors and the waveform generator 15.

As stated above, there are three main components required for the delivery of macromolecules into cells in tissue. They are a waveform generator 15, an electrode assembly holder 13, and a statically-coated electrode assembly 12. The waveform generator supplies the electrical pulses necessary for generating the electric field in the tissue. The electrode assembly 12 contains the electrodes 16, and the polynucleotide or protein macromolecules are applied to the electrodes 16 as a static coating. The electrode assembly holder 13 connects the electrode assembly 12 to the waveform generator 15.

The statically-coated electrode assembly 12 can be in the form of an electrode array can be in the form of a disposable, one-time-use electrode array which has the macromolecules pre-loaded onto the electrodes. In this respect, the pre-loaded electrode array can be provided as a sterile package. To use such an electrode array, the sterile package is opened, and the electrode array is connected to the electrode array holder. The electrode assembly holder is grasped by a person, and portions of the electrode assembly are forced into the selected tissue of a patient. For epidermal tissue, preferably, the tips of the electrodes in the statically-coated electrode assembly are located in the region of the Langerhans cells, which are dendritic cells of the epidermis.

Then, a pulse waveform is sent from the waveform generator, through the electrode assembly holder, and to the statically-coated electrode assembly. The pulse waveform drives pre-loaded macromolecules off of the statically-coated electrode assembly and into the epidermis. In the epidermis, the pulse waveform electropermeabilizes the target epidermal cells so that the macromolecules enter the target cells.

Figure 2:
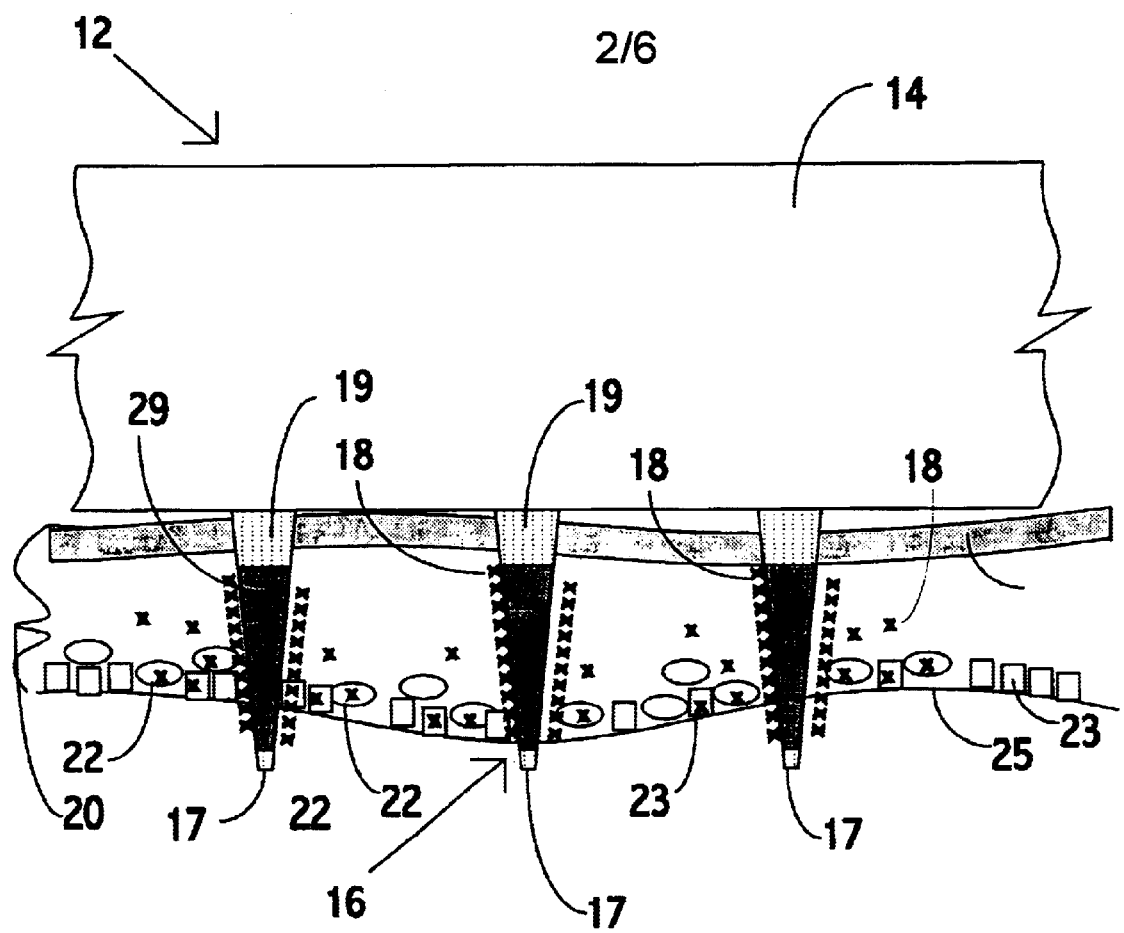
FIG. 2 is a schematic illustration of relatively short electrodes coated with a static layer of macromolecules, with the electrodes penetrating an epidermal skin layer, and with the macromolecules being driven by pulse waveforms of f of the electrodes to deliver macromolecules into epidermal cells.
Figure 3:
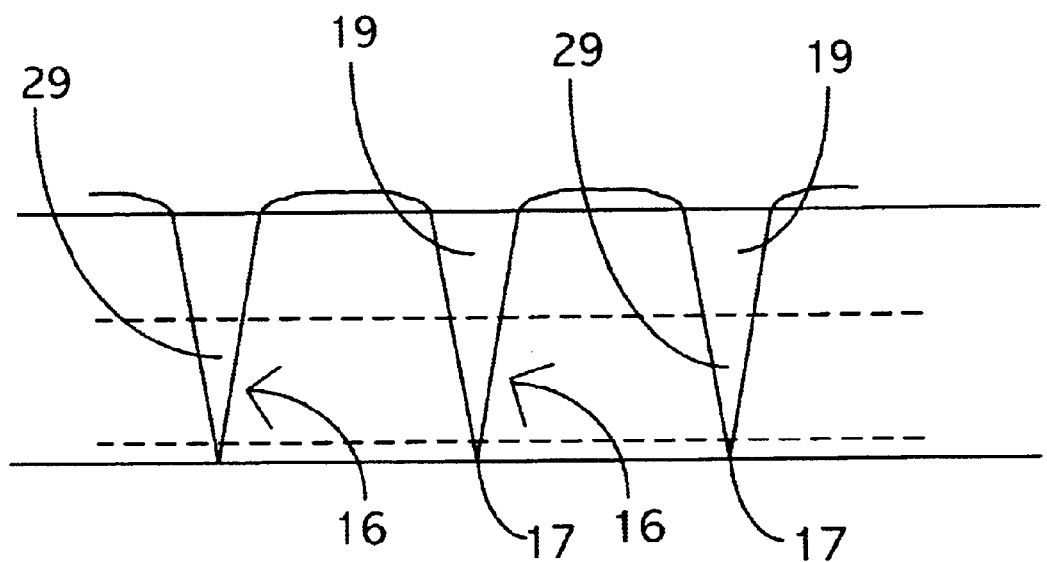
FIG. 3 is a schematic illustration of tip portions of the electrodes.
Figure 4:
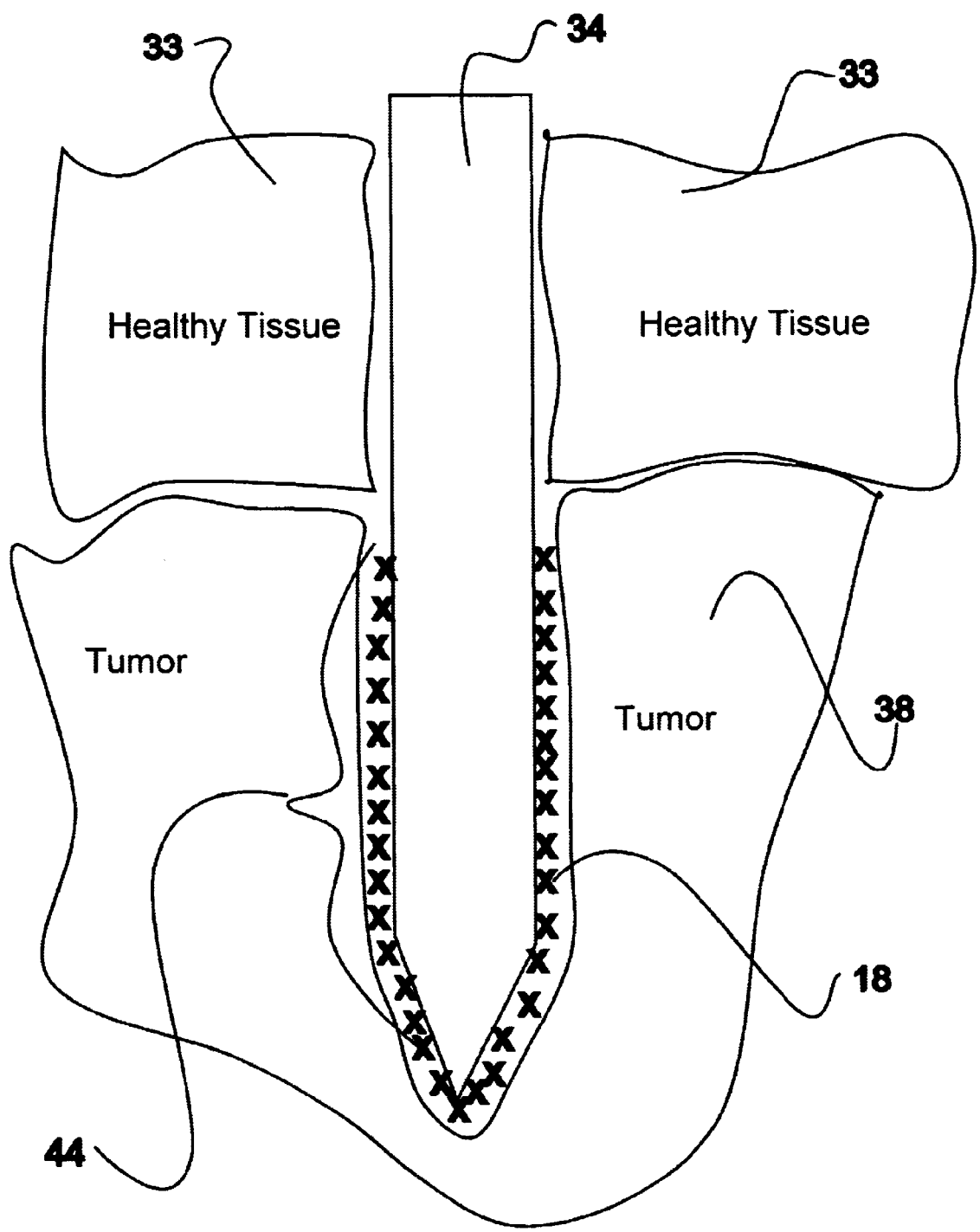
FIG. 4 is a schematic illustration of relatively long electrodes coated with a static layer of macromolecules, with the electrodes penetrating through healthy tissue into the tissue of a tumor.

As illustrated in FIG. 2, an electrode assembly 12 includes a non-conductive electrode carrier 14 and a plurality of individual needle electrodes 16 supported by the electrode carrier 14. The active areas 29 of the electrodes 16 are statically coated with macromolecules which are illustrated as small "x's" 18 on the surfaces of the electrodes 16. Under the influence of the pulse waveforms, some of the macromolecules 18 are driven off of the electrodes 16 by electrophoresis voltage and enter the epidermis 20 and are delivered to the dendritic Langerhans cells 22 and the living epithelial cells 23 in the living epidermis above the basal lamina 25 in the epidermis 20 by electroporation voltage.

The waveform generator 15 produces the pulses for the protocol. The output of the waveform generator can be conventional with a single selection of pulse parameters such as voltage, pulse width, interval between pulses, number of pulses and the vector of the pulse. Alternatively, the output of the waveform generator can be programmable with the ability to change any of the parameters (voltage, pulse width, interval between pulses, number of pulses,) from pulse to pulse. The variable output is needed for optimal performance because a different electric field is required for macromolecule movement off of the electrodes 16 than the electric field required for electric field mediated delivery of macromolecules into cells. A suitable programmable pulse generator is the PulseAgile (Registered in U.S. Patent and Trademark Office), Model PA-4000 Electroporation System made by Cyto Pulse Sciences, Inc., P. O. Box 609, Columbia, Md. 21045. It is noted that the Model PA-4000 delivers rectangular waves of various amplitudes (voltages), width, and intervals.

In addition to programmable control of voltage, pulse width, interval between pulses and number of pulses from pulse to pulse, programmable control of two other parameters is desired. One is control of the direction or vector of the applied electric field. The other is control of electrode selection. In one application, electric field direction could be reversed to insure better distribution of the macromolecule. In another application, individual pairs of electrode arrays could be sequentially selected.

A suitable device for electrode selection and the selection of electrode field direction is the programmable pulse switch, which is an optional component of the above-mentioned PA-4000 Electroporation System.

The statically-coated electrode assembly 12 serves two functions. It delivers the macromolecule to the desired site and it delivers the electric field to the tissue.

The statically-coated electrode assembly 12 includes:
1. a non-conductive electrode carrier 14.
2. an array of needle electrodes 16 fabricated on the electrode carrier 14, wherein the needle electrodes 16 are statically coated.
3. Electrode-assembly-conductive strips for electrical connection to the holder conductors on the electrode assembly holder 13 to connect electrically to the waveform generator 15.

In carrying out the method of the invention for epidermal use, the tips of the statically-coated needle electrodes 16 are pressed against the epidermis 20 of a patient with the needles puncturing the stratum corneum 27 and extending into the epidermis 20 and the upper dermis 31 as shown in FIG. 2.

The electrode needles can have many shapes. Examples of needle electrode shapes are: cylindrical needles, flat needles, cone shaped needles, and blade needles. The needles can be pointed rounded or blunt. Each of these shapes can be single or multiple per electrode row.

The purposes of the electrode assembly holder are to establish an electrical connection between the waveform generator and the electrode assembly and to provide a support for the electrode assembly when the electrode assembly is applied to the patient. It provides a mechanical connection for application to the patient. It also provides a means of delivering the electrode assembly to the patient's tissue while maintaining sterility of the electrode assembly.

The statically-coated electrode assembly can have the following optional features. It can have means to provide proper pressure on the electrode assembly to the tissue. It can have indicators that indicate correct application pressure, on-going electrical delivery, and completion of electrical delivery. It can have a switch for initiation of the pulse protocol. It can have a means for automatically initiating a pulse protocol when proper pressure is applied to the electrode assembly holder.

As stated above, macromolecules, including DNA and protein macromolecules, need to be driven off of the statically-coated coated electrodes 16 by electrophoresis voltages so that they can move through the extra-cellular spaces of tissue prior to the application of electroporation pulses for delivering the macromolecules into the targeted biological cells in the tissue.

As stated above, the macromolecules 18 in the static layer of electric field separable molecules 44 are initially bound to the fixed electrode surfaces 42 of the electrodes 16. In a mechanical approach to coating the electrodes 16 with a static coating of macromolecules 18, a relatively high concentration of macromolecules 18 is dissolved or suspended in a solvent or liquid carrier. The electrodes 16 are then dipped into the solution or suspension. Then, the solvent or liquid carrier is evaporated, leaving a static coating of macromolecules 18, in this case a solid coating of macromolecules 18, on the electrodes 16. Alternatively, the electrodes 16 are coated by spraying. Other mechanical means of coating the electrodes 16 are possible.

Macromolecules such as DNA bind with good efficiency to many surfaces. The physical and chemical properties of the material can be used to enhance binding to electrode surfaces to provide the statically-coated electrodes 16.

Molecules tend to bind to each other through various molecular interactions, each having a different binding strength. These same forces are active between solid substrates and soluble molecules as well as among molecules in solution. The molecular interactions are:

1. Solvation: Solvent binding. An interaction between the components of a molecule and the solvent molecules.
2. Hydrophobic interaction: A solute-solute interaction as a consequence of the inability to interact with the solvent; an avoidance interaction
3. Van der Walls forces are weak attractions that exist between all molecules. It is effective only at short distances and can be stronger if interactions based upon complementary shape
4. Hydrogen bonds are bonds formed between hydrogen and other molecules such as nitrogen and oxygen.
5. Ionic bonds are attractions based upon attraction of oppositely charged portions of molecules.
6. Covalent bonds are the strongest of molecular bonds.

More specifically with respect to DNA, DNA is both sparingly soluble in water and charged. The organic rings within the nucleotides impart the hydrophobic properties to DNA. The phosphate molecules in the DNA polymer, impart a net negative charge.

The strongest bond between an electrode surface and DNA is the hydrophobic bond. When an electrode has a positive charge, DNA moves towards the electrode thereby enhancing the interaction of DNA with the conductive hydrophobic surface. For delivery of the DNA to biological tissues, the electrical charge is reversed. Migration of macromolecules 18 from the electrode surface occurs as soon as the repelling force of like charges exceeds the force of the hydrophobic and other molecular interaction.

DNA can be coated onto specific sites by binding the DNA to metal (such as an electrode surface) or another conductive material through the use of a positive charge. Subsequently, for driving the DNA off of the electrode surface and for subsequently delivering the DNA to biological cells, a negative charge is applied to the same surface. DNA, being negatively charged, will migrate in an electric field toward the positive electrode. This phenomenon is called electrophoresis. If the positive electrode is a hydrophobic surface as are most metals, the positive charge and the hydrophobic interaction will work together to hold the DNA to the surface.

Most macromolecules have a net charge in solution at a pH other than its iso-electric point. DNA, for instance, is negatively charged at physiological pH. This means that a DNA molecule will migrate towards a positive electrode. This property is used to bring the macromolecule in contact with the electrode where binding of the DNA to the electrode surfaces occurs via the other molecular interactions listed. DNA, for instance, can bind because it is hydrophobic.

Figure 6:
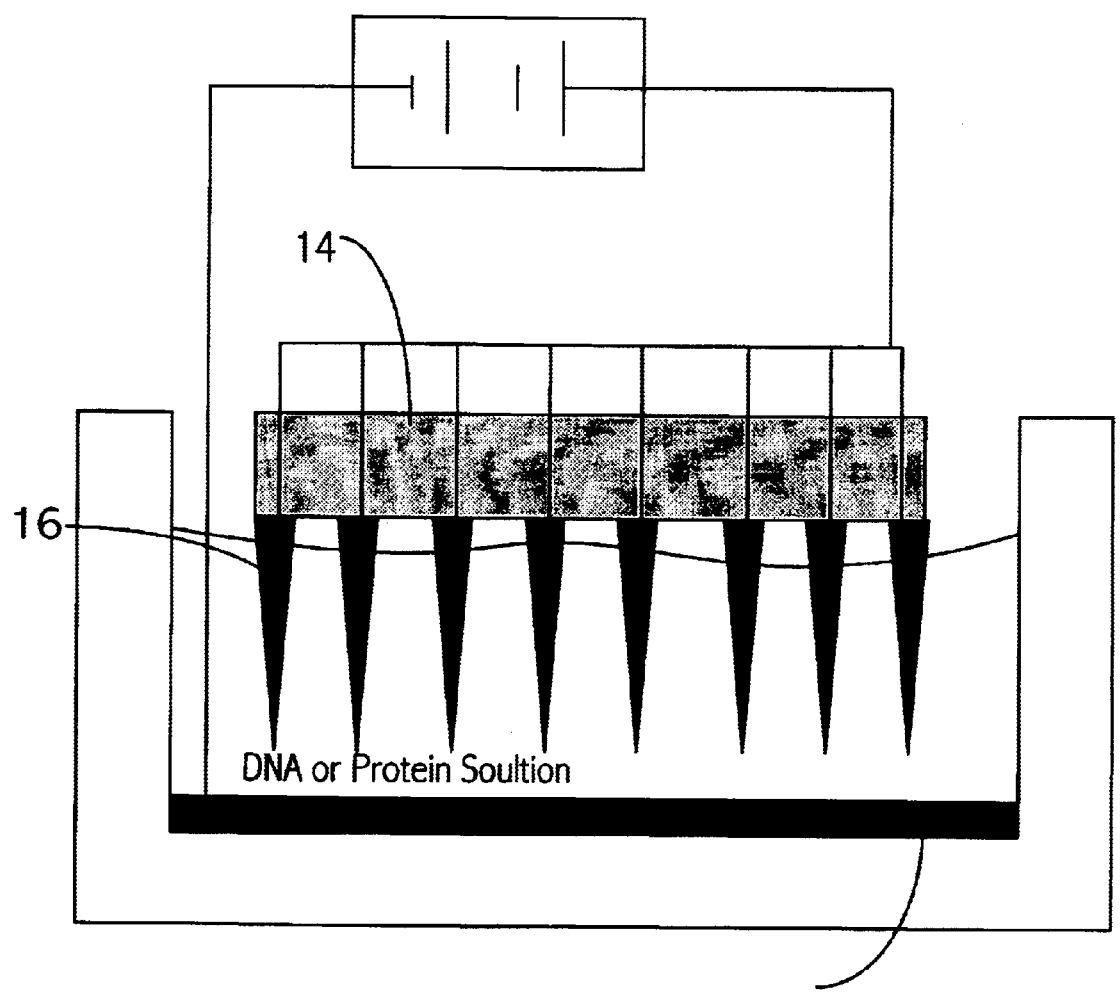
FIG. 6 schematically shows apparatus used for coating the electrodes with macromolecules.

Electrical coating takes advantage of the charge of the macromolecules. A stated above, DNA is negatively charged and therefore migrates to a positively charged electrode. Reference is made to FIG. 6 which illustrates an apparatus used for coating the electrodes 16 with a static coating. In one coating process, DNA is added to a buffer solution and then placed into a chamber with an electrode that serves as the cathode. Preferably this electrode is separated from the buffer by a gel interface to prevent metal of the cathode coming into contact with the DNA. The electrode device is inserted into the liquid, and a positive charge is applied to the electrode device drawing the DNA to the surface of the electrode device. The DNA attaches to the surface of the electrode device by hydrophobic or other interaction to provide a statically-coated electrode until the DNA is expelled by a reverse charge. The DNA is dried on to the device with or without a protectant, such as sugars, and with or without other carrier molecules. Substances can also be added to the static coating on the electrodes which promote uptake of the treating material into the target cells.

The amount of statically-coated macromolecule on the electrode assembly varies depending upon the application. For DNA immunization, for example, the electrode assembly is loaded with 0.01 to 100 micrograms of plasmid DNA.

Sterile materials and a sterile local environment can be used in the manufacture of the electrode assembly with the macromolecule. Alternatively, the assembly can be sterilized after manufacture.

A typical sequence of steps in administering macromolecules 18 to a patient using the method and apparatus of the invention are described as follows. In a clinic, the waveform generator 15 would be connected to the electrode assembly holder 13. For an individual application, an electrode assembly 12 whose electrodes 16 have been loaded with a static coating of the desired macromolecule is selected. The electrode assembly 12 is then mechanically connected to the electrode assembly holder 13. As the electrode assembly holder 13 is grasped by an operator, the statically-coated electrodes 16 are pressed onto the patient's tissue (e. g. skin). For skin, the statically-coated electrodes 16 penetrate into the epidermis 20 and extend substantially only to the basal lamina layer. After the statically-coated electrodes 16 have been located thusly in the epidermis 20, the macromolecular delivery process is started, and the selected pattern of electric fields is initiated. After completion of the delivery protocol, the electrodes 16 are removed from the epidermis 20, and the electrode assembly 12 is discarded.

As stated above, when a solvent separable solid material is not employed in the electrode releasable molecules 44, the electrical protocol is designed to drive the statically-coated macromolecules off of the electrodes 16 into the tissue, followed by delivery of the macromolecules into cells in the tissue. For DNA, a typical sequence of electrical pulses is as follows. First, a series of low voltage (electrophoresis) pulses are applied to the electrodes 16 to remove the DNA from all negatively charged electrodes. Typically, alternating rows of electrodes are negatively charged. Next, higher voltage electroporation pulses are applied to the electrodes 16 to drive the DNA into cells. Next, electrode polarity is reversed and low voltage pulses delivered with opposite polarity to remove the DNA from the remaining electrodes. Higher voltage electroporation pulses are then applied to force the DNA into cells.

A significant use of this macromolecular delivery system is to deliver macromolecules to skin. For this use, electrode needle length is chosen to allow penetration of the electrode to the stratum basalis and basement membrane (basal lamina). Some slight penetration into the dermis may occur. For this use on a patient's arm, an electrode length of 130 microns is selected. This depth allows treatment of cells of the epidermis. For a DNA vaccine or gene therapy, the cells transfected by this delivery method are dendritic cells (skin Langerhans cells 22) and epithelial cells.

Aside from administering macromolecules to biological cells in the epidermis, the method and apparatus of the invention can be used in other biological environments, such as tissues during surgery and with plants.

A wide variety of methods can be employed for manufacturing the electrode assembly 12 of the invention, prior to application of the static coating. A number of examples are presented below.

Standard microchip manufacturing processes can be adapted to make the conductive microneedles on a non-conductive support, as in accordance with the invention. In one example, a blank consisting of a silicon or other non-conductive layer and a metal layer would be used. The mask would be designed to encourage more etching between rows than within rows, resulting in conductive rows of electrodes with nonconductive spaces between rows.

Another method of construction of an electrode assembly is by adapting the known technique of extrusion microfabrication, and an example follows. Electrode material and adjacent insulating material are prepared by mixing a ceramic, metal or other powder with a thermoplastic binder. The individual components are assembled and warm pressed to stick together. The resulting rod is extruded to reduce its size. Following the extrusion, the new rods are assembled in a rod composed of a multiple of the extruded rod. This newest rod is re-extruded to reduce the size of the multiple rods to the size of the first extruded rod. After the size is reduced to the desired size the parts can be heated to remove the binder. A second, higher heat is used to sinter the metal or ceramic powders together. The rods are cut into disks before or after the sintering. Differential sand blasting or other mechanical or chemical techniques can be used to raise the needles above the surface of the insulator.

Another method for manufacture would be to use laser milling techniques to remove material from a sandwich composed of conductive and nonconductive layers.

For some of the arrays of electrodes, the distance between the electrodes is large enough for mechanical assembly. An example of such assembly follows. Wire of the desired metal composition and diameter is arranged on spools for assembly. The wires are fed into an apparatus that aligns the wire to the correct distance apart. Ceramic or plastic material is injected into a flow through system that results in complete filling of the gap between the electrodes and forms the shape of the outside rim of the electrode. The plastic or ceramic is hardened and cut into discs. The resulting disks are differentially eroded, taking advantage of the softer matrix. The erosion can be done using mechanical methods, chemical methods or a combination of methods. The surface erosion leaves needles of the desired length protruding above the supporting matrix.

Another manufacturing technique for an electrode assembly is described as follows. Stainless steel needles 30 mm in length and 120 microns in diameter are obtained. One source is from an acupuncture supply company. Seirin No. 02 needles are an example. The needles are cut from the handle if one is present. A number of needles are selected for each row of the device. Thirty-five needles per row are used for this example. The needles are carefully placed side by side with the tips of the needles in line. This step requires care and a jig made of a microscope slide glued at 90 degrees on top of another microscope slide is a tool to help in the alignment. The slide also is be used to check the alignment on a microscope. The needle row (needle bundle) is taped together with 50 micron thick tape. Two or more of the needle bundles are stacked to form an electrode array with the tips of each bundle aligned with the next bundle. The needles are silver soldered to a wire, and alternating needle bundles are connected together electrically. An overall support structure is provided to support the electrode array of needle bundles.

As example of making an electrode assembly which includes long needles is as follows. One embodiment of long needle electrodes can be made in the following manner. Several ⅛ inch thick Lexan sheets are cut to the dimension of 1 cm by 1.5 cm. Two parallel rows are markded 5 mm apart. Drill points 2 mm apart are marked along each of the parallel lines that are 5 mm apart. Holes are drilled at each marked point, 0.35 mm in diameter.

Stainless-steel acupuncture needles, such as Seirin No. 8 needles, are selected. Needles are inserted through one of the three Lexan pieces. Lengths of nickel capillary tube, 2 mm in length, are cut wherein the capillary tube has an inner diameter of 0.020 inches. A cut capillary tube is slid onto each of the needles. Needles are inserted through the remaining two of the Lexan pieces. The Lexan piece nearest the points is placed on a spacer that leaves 0.5 cm of needle extending beyond the Lexan piece. Using an epoxy adhesive, the needles are fixed in place to the Lexan piece nearest the point. The second piece is moved 0.5 cm from the first piece. The space formed by three sides between the two Lexan pieces is sealed, and a high heat plastic or epoxy is poured in to fill the space. The nickel pieces are soldered to the stainless steel by filling the space between the nickel tubing and the needle. A high-voltage wire is soldered to connect one of the rows of needles at the site of the nickel capillary tubing. A high-voltage wire is soldered to the other row of needles at the site of the nickel capillary tubing. The space between the last two Lexan pieces is sealed on three sides, and the space is filled with a high heat epoxy. The acupuncture needle handles are removed, and the needles are rinsed to a point flush with the top of the last Lexan piece. The top is sealed with an electrically resistant epoxy. Banana plugs are placed on the other end of the high-voltage wires. The needles can be insulated by adding a small amount of epoxy or Teflon paint to the ends of the needles. In addition, other selected areas of the needle may be insulated.

The long-needle electrodes can be coated in many ways. The following is one method. The needles are immersed in a solution of DNA that has 0.3 micrograms per microliter of DNA in a TE buffer. The needles are suspended in the solution without touching the bottom of the container. The container holding the liquid has a stainless-steel bottom that serves as a negative electrode. All of the needles are then connected to a common positive pole of a power supply. A voltage of 1.5 V is applied to the needles for several minutes. The needles are then removed from the solution and can be used immediately because the DNA forms a static coating on the electrodes. Alternatively the DNA can be dried on the needles. A statically-coated protectant such as sucrose may be added to the needles by dipping in a sucrose solution prior to drying the DNA.

The capacity of the needles for retaining statically-coated surface DNA can be extended in several methods. One method is simply to apply multiple layers of statically-coated DNA to the surface of the needles. Another method is to make the surface area of the needle greater by adding a porous sintered metal surface. Another method is to add a polymer or a gel to the electrode surface to provide a three-dimensional surface to the metal electrode surface for the statically-coated DNA to adhere to.

The statically-coated DNA can be protected from the influence of environmental DNAses by embedding the DNA in liposomes, adding DNAse inhibitors or coating the needle in a protectant. Sterile, desiccated packaging will also protect the statically-coated needles.

An example of using statically-coated, long needle electrodes is described as follows. The needle electrodes containing the statically-coated DNA are inserted into tissue for use. The small voltage electrophoretic potential may be applied for a period of seconds to minutes to move the DNA off of the needles and into the tissue. Electroporation pulses can then be added to drive the DNA into cells of the tissue. More electrophoretic pulses may be needed to help move the DNA into cells. After a resting period of several seconds, polarities can be reversed on the needles and the same protocol can be repeated.

In accordance with another aspect of the invention, polymers can be used to modify adhesion of DNA to metal electrodes. As described above, DNA can be coated onto a metal electrode surface using electric charge to facilitate the binding of the DNA to the electrode surface. However, such a DNA binding can be a high affinity binding which makes driving the DNA off from the electrode using electric fields difficult. Consequently, in accordance with the invention, methods are provided for controlling the adhesion of DNA to fixed electrode surface 42 and easing the release of DNA from the fixed electrode surface 42 using electric fields.

In accordance with an aspect of the invention, a water-insoluble adhesion controlling polymer 52 can be coated onto the electrode underbody 40 to form the fixed electrode surface 42. Then, the electrode releasable molecules 44 are coated onto the fixed-surface adhesion controlling polymer 52. In such a case, when the electrodes are placed next to the biological cells, the water-insoluble adhesion controlling polymer 52 remains fixed on the electrode underbody 40, and the electrode releasable molecules 44, which are electric field separable molecules, are driven off of the water-insoluble adhesion controlling polymer 52.

Also, in accordance with an aspect of the invention, a water-insoluble adhesion controlling polymer 52 can be mixed together with electrode releasable molecules 44, and the mixture can be coated onto the electrode underbody 40 to form a fixed electrode surface 42 which is intermingled with the electrode releasable molecules 44. In such a case, when the electrodes are placed next to the biological cells, the water-insoluble adhesion controlling polymer 52 remains fixed on the electrode underbody 40, and the intermingled electrode releasable molecules 44, which are electric field separable molecules, are driven off of the water-insoluble adhesion controlling polymer 52 and driven into the biological cells.

Alternatively, in accordance with the invention, the adhesion controlling polymer 52 can be water soluble and can be applied to the surface of the electrode underbody 40 which serves as the fixed electrode surface 42. Then, the electrode releasable molecules 44 are coated onto the adhesion controlling polymer 52. In such a case, when the electrodes are placed next to the biological cells, the water-soluble adhesion controlling polymer 52 is dissolved by the body fluids, and both the water-soluble adhesion controlling polymer 52 and the electrode releasable molecules 44 are released from the fixed electrode surface 42. Under the influence of applied electric fields, the electrode releasable molecules 44 are driven into the biological cells.

Alternatively, in accordance with the invention, the adhesion controlling polymer 52 can be water soluble and can be mixed with the electrode releasable molecules 44. The mixture is applied to the surface of the electrode underbody 40 which serves as the fixed electrode surface 42. In such a case, when the electrodes are placed next to the biological cells, the water-soluble adhesion controlling polymer 52 is dissolved by the body fluids, and both the water-soluble adhesion controlling polymer 52 and the electrode releasable molecules 44 are released from the fixed electrode surface 42. Under the influence of applied electric fields, the electrode releasable molecules 44 are driven into the biological cells.

Alternatively, all of the following can be used to coat the electrode underbody 40: a water-insoluble adhesion controlling polymer 52, a water soluble adhesion controlling polymer 52, and electrode releasable molecules 44. In such a case, the water-insoluble molecules remained fixed on the fixed electrode surface 42, and the water-soluble adhesion controlling polymer 52 and the electrode releasable molecules 44 are released from the fixed electrode surface 42 when the electrodes are placed next to the biological cells. The electric fields then drive the electrode releasable molecules 44 into the biological cells.

In general, in one class of methods, polymers are added to the electrode underbody 40 prior to applying the electrode releasable molecules 44, e. g. DNA. In another class of methods, polymers are mixed with electrode releasable molecules 44, e. g. DNA, prior to coating the electrode underbody 40 with the mixture.

For in vivo delivery of DNA, the polymer needs to be biocompatible. A partial list of biocompatible polymers follows: poly(vinyl alcohol), poly(methacrylic acid), poly (ethoxazoline), poly(hydroxybutyrate), poly(caprolactone), poly(2-hydroxymethacrylate) and poly(acrylic acid). Co-polymers with components of these polymers may also be biocompatible. Many other polymers are biocompatible and may be appropriate for use.

Co-polymers may be especially useful if modified properties are desired. For example, the addition of segments of cationic polymers in non-ionic polymers may promote binding of DNA to the polymer. Other ionic co-polymers may be used to impart an environmental sensitivity to the polymer. Examples are pH sensitivity, temperature sensitivity, chemical sensitivity, solvent sensitivity or electric field sensitivity. All of these modifications can be used to control the release of biopolymers (DNA, RNA, proteins) mixed with or associated with the additional polymer on the surface of an electrode.

One example of the use of a polymer to assist loading of DNA onto a needle surface is as follows: Poly vinyl alcohol is dissolved in water by heating. The amount of polymer used in this example is a 2% polymer in water (w/v). The electrode is dipped in the polymer and the electrode is dried at 70 degrees centigrade. Next, 10 microliters of DNA at 2.5 micrograms per microliter is added to the needle surface by pipetting. The DNA is dried onto the surface at 70 degrees centigrade. This process can be done in one step by mixing the DNA and polymer prior to application. The needle electrode is then stored dry until used. Another advantage of adding polymers to electrode metal surfaces with the DNA is to reduce electrolysis at electrode surfaces touching cells and DNA. A polymer that remains on the metal surface as a hydrated polymer can keep the metal separated from living cells and from the DNA. Such a polymer separates electrode surfaces, which may have sites with active surface electrolysis, from the living cells and from the DNA, thereby reducing the chance of damage to either the cells or the DNA.

Even if polymers are used to assist in initial release of biopolymers, e. g. DNA, from the surface of the electrode, pulsed electric fields are still needed for subsequent phases of the delivery of the biopolymers into the biological cells. Pulses whose main purpose is electrophoresis may be used to move the biopolymer from next to the needle electrode to surrounding tissue. An electroporation pulse is needed to make the surrounding cells permeable to the biopolymers. And an additional set of pulses, used for electrophoresis, may be needed to move the biopolymer into the cells.

Although aspects of the invention have been described hereinabove in greater detail, here is a relatively brief review of aspects of the invention.

A method is provided for delivery of molecules into biological cells. The method includes providing electrodes in an electrode assembly wherein the electrodes have fixed electrode surfaces which are coated with at least one static layer of electric field separable molecules to be delivered. A waveform generator is provided for generating electric fields, and electrically conductive pathways are established between the electrodes and the waveform generator. The electrode assembly having the statically coated electrodes can be attached to an electrode assembly holder for establishing electrically conductive pathways between the electrodes and the waveform generator. The electrodes are located such that the biological cells are situated therebetween, and electric fields are provided in the form of pulse waveforms from the waveform generator to the electrodes, such that molecules in the at least one static layer of the electric field separable molecules on the electrodes are driven off of the electrodes and delivered into the biological cells.

An electrode surface itself can serve as the fixed electrode surface. The fixed electrode surface can include an oxidized metal surface. The oxidized metal surface can include an oxide of silver, an oxide of nickel, or an oxide of copper. The fixed electrode surface can include fixed metal particles, or a roughened surface.

The electric field separable material on the fixed electrode surface can include a gel coating, a solid layer of nonpolymeric material, or a polymer layer.

In accordance with another aspect of the invention, a method is provided for immunotherapy which includes the steps of (a) obtaining statically-coated electrodes which are statically-coated with an immuno-stimulating material, (b) inserting the statically-coated electrodes into a tissue to be treated, (c) applying electrophertic and electroporation pulses to the statically-coated electrodes such that the immuno-stimulating material is driven off of the statically-coated electrodes and into cells in the tissue.

In accordance with another aspect of the invention, an electrode is provided which includes a coating having at least one static layer of electric field separable molecules to be delivered into biological cells. The electrode can include a fixed electrode surface which is coated with the static layer of electric field separable molecules. The molecules in the static coating can be in a solid phase, a gel.

The fixed electrode surface 42 can include a fixed surface matrix, and the molecules in the static coating are in a liquid fixed on the fixed surface matrix. The fixed surface matrix can include solid surface particles. The solid surface particles can be metal particles. The fixed surface matrix can include a liposome matrix or a solid polymer matrix.

The molecules in the static coating can be macromolecules, and the macromolecules can include a polynucleotide vaccine, such as a solid phase polynucleotide vaccine, a DNA vaccine, a solid phase DNA vaccine, a RNA vaccine, or a solid phase RNA vaccine. The macromolecules in the static coating can include a protein-based vaccine, such as a solid phase protein-based vaccine. The macromolecules in the static coating can include an organ treating agent. The organ treating agent can include a deep tumor tissue treating agent.

The electrode can be in a form of a needle electrode.

In accordance with another aspect of the invention, the coating of the electrode by the static coating molecules is carried out by the following steps: preparing a liquid medium in which a quantity of the molecules are carried; contacting the electrodes with the prepared medium; removing the electrodes from the medium; and drying off the medium, such that a static coating of the molecules remains on the electrodes.

In accordance with another aspect of the invention, the coating of the electrode by the static coating molecules is carried out by the following steps: preparing a liquid medium in which a quantity of the molecules are carried; contacting the electrodes with the prepared medium; applying pulse waveforms to the electrode, such that a portion of the molecules are bound to the electrode; removing the electrode from the medium; and drying off the medium, such that a coating of the molecules remains on the electrode.

In accordance with another aspect of the invention, an apparatus is provided for delivery of molecules into biological cells. The apparatus includes a waveform generator which provides pulse waveforms. An electrode assembly holder is provided, and an electrode assembly having a plurality of electrodes is mechanically supported by an electrode assembly holder. The electrode assembly is electrically connected to the waveform generator through electrically conductive pathways. The electrode assembly includes electrodes which are coated with at least one static layer of molecules to be delivered into the biological cells.

It is apparent from the above that the present invention accomplishes all of the objects set forth by providing a method and an apparatus for delivery of macromolecules into cells that do not cause skin damage that results in scarring. With the invention, a method and an apparatus for delivery of macromolecules into cells are provided which do not leave a residue of ballistic particles in cells that are treated. With the invention, an electroporation method for delivering molecules to biological cells in the epidermis, near the basal lamina, does not have the treatment molecules pass through the skin transdermally. With the invention, a method and an apparatus for delivery of macromolecules into cells are provided which do not employ a hypodermic needle. With the invention, a method and an apparatus for delivery of macromolecules into cells are provided which do not employ a fluid medium that flows down onto the electrodes as the electroporation process is being carried out on the patient.

With the invention, a method and an apparatus for delivery of macromolecules into cells are provided which do not employ a pressurized fluid injection step for injecting fluid into a patient. With the invention, relatively low absolute voltages are applied to cells undergoing electroporation. With the invention, pulses that are applied to the cells can have, if desired, relatively short pulse width to the cells undergoing electroporation. With the invention, a method and an apparatus for delivery of macromolecules into cells are provided which can employ, if desired, electrodes in which the base portions and tip portions of the electrodes are nonconductive. With the invention, a method and an apparatus for delivery of macromolecules into cells provide disposable electrode assemblies. With the invention, a method and an apparatus for delivery of macromolecules into cells are provided in which electrode assemblies are packaged in sterile packaging. With the invention, a method and an apparatus for delivery of macromolecules into cells are provided which permit treatment of tissues using coated long electrodes which have electric field separable material which includes a tissue treating agent.

What is claimed is:

1. A method for delivery of molecules into biological cells, comprising the steps of:
    obtaining electrodes in an electrode assembly, wherein the electrodes have fixed electrode surfaces which are coated with at least one static layer of electrode releasable molecules to be delivered,
    obtaining a waveform generator for generating electric fields,
    establishing electrically conductive pathways between the electrodes and the waveform generators
    locating the electrodes such that the biological cells are situated therebetween, and
    providing electric fields in the form of pulse waveforms from the waveform generator to the electrodes, such that molecules in the at least one static layer of the electrode releasable molecules on the electrodes are delivered into the biological cells.

2. The method of claim 1, further including the step of attaching the electrode assembly having the statically coated electrodes to an electrode assembly holder for establishing electrically conductive pathways between the electrodes and the waveform generator.

3. The method of claim 1 wherein the electrode releasable molecules 44 include electric field separable molecules.

4. The method of claim 1 wherein the electrode releasable molecules 44 include solvent separable material that is separable from the electrode, by a solvent.

5. The method of claim 1 wherein the electrode releasable molecule 44 include electric field separable molecules and solvent separable material that is separable from the electrodes by a solvent.

6. The method of claim 1 wherein the fixed electrode surfaces 42 includes a water-insoluble polymer.

7. The method of claim 1 wherein the fixed electrode surfaces 42 include a water-insoluble polymer and a water-soluble polymer.

8. The method of claim 1 wherein an electrode surface itself serves as a fixed electrode surface.

9. The method of claim 1 wherein the fixed electrode surfaces include an oxidized metal surface.

10. The method of claim 1 wherein the fixed electrode surfaces include fixed metal particles.

11. The method of claim 1 wherein the fixed electrode surfaces include roughened surfaces.

12. The method of claim 1 wherein the electrode releasable molecules on the fixed electrode surfaces include a gel coating.

13. The method of claim 1 wherein the electrode releasable molecules on the fixed electrode surfaces include a solid nonpolymeric material.

14. The method of claim 1 wherein the electrode releasable molecules on the fixed electrode surfaces include a polymer.

15. A method for treating tissue cells, including the steps of:
    (a) obtaining statically-coated electrodes which are statically-coated with molecule of an electrode releasable tissue treating agent,
    (b) inserting the statically-coated electrodes into a tissue to be treated,
    (c) releasing molecules of the electrode releasable tissue treating agent from the electrode, and
    (d) applying electroporation pulses to the electrodes such that the released molecules of the electrode releasable tissue treating agent are driven into cells in the tissue.

16. The method of claim 15 wherein the tissue to be treated is skin tissue.

17. The method of claim 15 wherein the tissue to be treated is deep organ tissue.

18. The method of claim 15 wherein the tissue to be treated is muscle tissue.

19. The method of claim 15 wherein the molecules of the electrode releasable tissue treating agent are released from the electrodes by applying electrophoretic pulses to the electrodes.

20. The method of claim 15 wherein the molecules of the electrode releasable tissue treating agent are released from the electrodes by contacting the electrodes with a solvent.

21. A method for immunotherapy, including the steps of:
    (a) obtaining statically-coated electrodes which are statically-coated with an immuno-stimulating material,
    (b) inserting the statically-coated electrodes into a tissue to be treated,
    (c) releasing the immuno-stimulating material from the electrode, and
    (d) applying electroporation pulse to the electrodes such that the released immuno-stimulating material is driven into cell in the tissue.

22. The method of claim 21 wherein the immunostimulating material is released from the electrodes by applying electrophoratic pulses to the electrodes.

23. The method of claim 21 wherein the immunostimulating material is released from the electrodes by contacting the electrodes with a solvent.

24. The method of claim 21 wherein the immunostimulating material is released from the electrodes by contacting the electrode with a solvent which includes body fluids.

* * * * *